United States Patent [19]

Marinoff

[11] 4,275,733
[45] Jun. 30, 1981

[54] OPHTHALMOLOGICAL SURGICAL INSTRUMENT

[76] Inventor: Gerald P. Marinoff, 8 Rockford Dr., West Nyack, N.Y. 10999

[21] Appl. No.: 86,816

[22] Filed: Oct. 22, 1979

[51] Int. Cl.³ .............................................. A61B 17/00
[52] U.S. Cl. ................................................ 128/303 R
[58] Field of Search ........... 128/17, 20, 303 R, 334 R, 128/337

[56] References Cited

FOREIGN PATENT DOCUMENTS 2354752  1/1978  France ................................. 128/303 R
303071  8/1971  U.S.S.R. ............................... 128/303 R

OTHER PUBLICATIONS

Fibra-Sonics, "Introducing the G-15E/RA/IIA Lens Fragmentor/Aspirator" (1977).

*Primary Examiner*—Robert W. Michell
*Assistant Examiner*—Michael H. Thaler
*Attorney, Agent, or Firm*—Arthur Dresner

[57] ABSTRACT

The ophthalmological surgical instrument of the present invention is used for stabilizing a patient's eye to prevent inward collapse during ophthalmic surgery. The instrument generally includes a ring which is adapted to be placed on the surface of the eye surrounding the cornea. A plurality of securing devices are permanently carried by the ring being circumferentially and equally spaced about the ring to temporarily secure the ring to the surface of the eye. With the ring secured to the eye the integrity of the eye will be maintained regardless of any incisions made in the eye or sections which may be removed therefrom.

7 Claims, 3 Drawing Figures

OPHTHALMOLOGICAL SURGICAL INSTRUMENT

BACKGROUND OF THE INVENTION

The present invention relates generally to the field of surgical instruments and more particularly is directed toward an instrument which is used during ophthalmic surgery to prevent inward collapse of the eye during various surgical procedures.

In typical corneal transplant surgery a section of the eye involving the diseased cornea is removed for replacement by a healthy section. Removal of the diseased section is accomplished by performing a circular incision to a desired depth so that a cylindrical or truncated pyramidal section or plug can be removed. After removing the plug or section a bore-like hole remains for reception of a healthy section or plug which is similarly cut from a donor eye. The circular incision to form the cylindrical or pyramidal section is typically accomplished through the use of corneal trephines or other surgical incision making tools.

During the period between removal of the diseased section and insertion of the healthy section there is the possible danger of the walls of the bore-like opening collapsing inwardly.

Similarly, in surgical procedures to remove cataract lenses it is typical procedure for the surgeon to form a semicircular groove in and about the limbus area of the eye which the surgeon then uses to cut through the eye thus forming a flap to provide access to the anterior chamber of the eye so that the cataract lens may be removed. The formation of the flap which is lifted to provide access to the lens again presents possible danger of collapse of the eye.

In order to overcome the problem of eye collapse during the aforementioned types of ophthalmic surgery, some surgeons have adopted a procedure of suturing a stainless steel ring to the surface of the eye prior to making an incision. Rings of this type (sometimes referred to as a "Flieringa ring") are commercially available, such as for example from the Storz Surgical Instrument Company (catalog number E-4034). The commercially available rings are usually of a diameter such that they will be placed in a position surrounding the cornea so that the surgical procedure takes place radially within the ring.

It is generally accepted that the use of the ring facilitates more accurate wound closure and tends to reduce postoperative astigmatism. At present the only means of securing the ring to the eye is to use a plurality of sutures which pass through the surface of the eye and around the ring. However, before the sutures can be placed, either separate incisions through the conjunctiva must be made, or a 360° conjunctival peritomy is made at the limbus or a combination of separate incisions and peritomy must be made. The conjunctiva can then be dissected back by about 5 millimeters. The ring can then be placed outside the limbus and within the conjunctiva, and sutured to the scleral tissue preferably at 90° intervals between the tendons of the four rectus muscles. This will usually allow sufficient room between the limbus and the ring to perform appropriate surgical procedures.

Because however the use of the ring requires additional delicate surgery and suturing many surgeons fail to take advantage of the benefits afforded by the use of preplacing a ring prior to ophthalmic surgery. Additional incisions to the conjunctiva and placing sutures in the sclera with a high risk of perforation are time consuming and present additional dangers to the patient. Furthermore, the areas for suturing are often difficult to reach with a needle holder. Therefore, many surgeons tend to avoid preplacement of the ring.

It is accordingly the principal object of the present invention to provide a surgical instrument which obviates the foregoing disadvantages in using the Flieringa ring.

A more specific object of the present invention is to provide a ringed type device which simplifies the procedure for attachment to the eye so as to make the use of the ring more acceptable to the surgeon.

Yet a further object of the present invention is to provide a ring having a plurality of securing devices permanently carried by the ring so as to facilitate easy and rapid attachment and detachment of the ring to the eye.

Other objects, features and advantages of the present invention will become more apparent to those skilled in the art from the detailed description of the invention in conjunction with the accompanying drawings to be described more fully hereinafter.

SUMMARY OF THE INVENTION

The foregoing objects of the present invention are generally accomplished by providing an ophthalmalogical surgical instrument for stabilizing the eye of a patient during ophthalmic surgery which includes a ring adapted to be placed on the surface of the eye circumventing the cornea, and a plurality of securing devices permanently carried by the ring and circumferentially spaced about the ring for temporarily securing the ring to the surface of the eye, so that the ring will support the integrity of the eye regardless of incisions made therein.

The foregoing and other features of the present invention are more fully described with reference to the following drawings annexed hereto.

DESCRIPTION OF THE INVENTION

Figure 1:
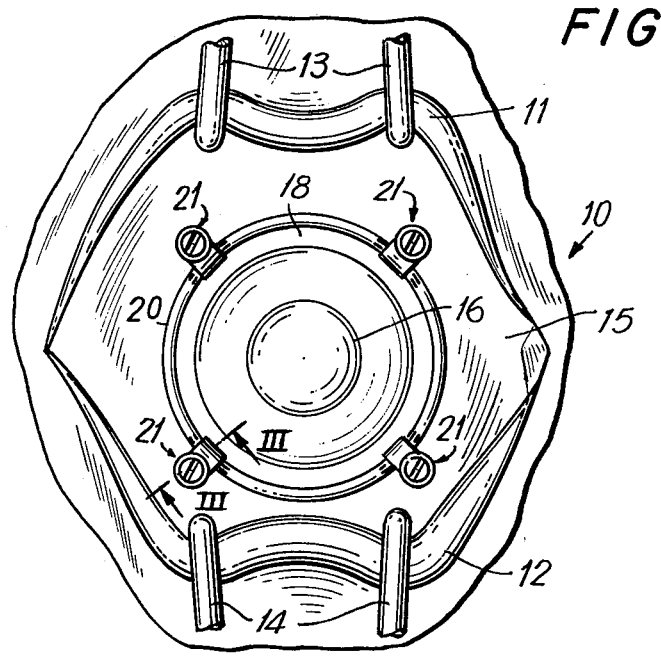
FIG. 1 is a plan view of the globe of the eye with eyelids shown in a retracted position and illustrating the present invention in plan view when placed in a position for use on the eye.

Referring now in greater detail to the accompanying drawings, FIG. 1 shows in plan view a representation of a human eye as prepared for surgery. The eye, indicated generally by reference numeral 10 includes upper and lower eyelids 11 and 12 respectively which are held in a retracted position by a pair of commonly used lid retractors thirteen and fourteen. The lid retractors are commercially available such as from the Storz Surgical Instrument Company under Catalog Nos. E-996, E-997, E-998 or E-1000. Retraction of the eyelids reveals a major portion of the globe 15 of the human eye so as to provide sufficient room for the surgeon to prepare the eye for the surgical procedure.

The present invention includes a ring portion 20 and at least four securing devices 21 permanently carried by the ring portion 20. In the embodiment illustrated herein, four such securing devices are illustrated as being spaced at approximately 90° intervals about the ring. While four securing devices are shown, the invention could operate with only 3 such devices as well. As can be appreciated from FIG. 1, the ring is circumferentially spaced about the cornea 16 concentric with the limbus area 18. A ring having an approximate diameter of 16 millimeters will be placed in the position shown in FIG. 1. Other sized rings can, of course, also be used.

Figure 2:
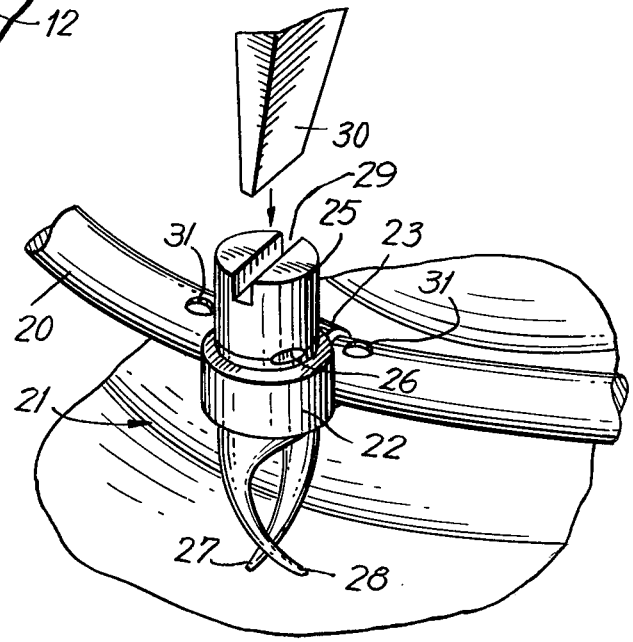
FIG. 2 is a perspective view of a portion of the ring illustrating in greater detail one of the securing devices carried by the ring.
Figure 3:
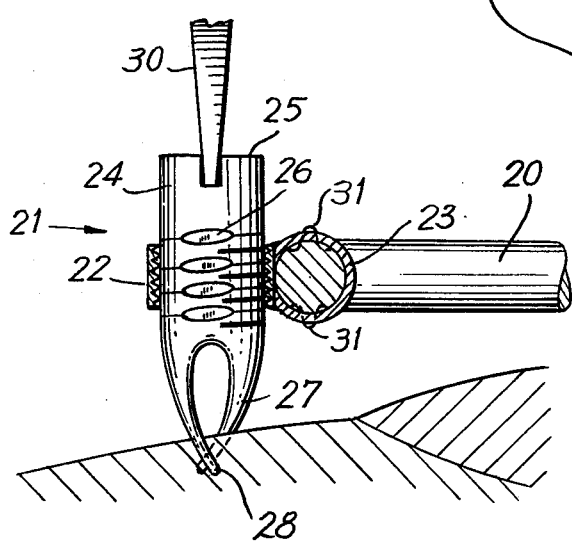
FIG. 3 is a sectional view taken along lines III—III in FIG. 1.

The securing devices 21 are shown in greater detail in FIGS. 2 and 3. Each such device includes an internally threaded cylinder 22 which is carried for pivotal movement about ring portion 20 on sleeve 23. A twist fixator 24 having a plurality of non-slip threads 26 externally arranged on a shaft portion 25, is arranged within the threaded cylinder 22. The twist fixator carries a pair of prongs 27 and 28 extending downwardly and along a curved path from the shaft portion 25 approximately between 0.3 millimeters and 0.5 millimeters. The prongs 27 and 28 are curved in opposite directions so that when the fixator is twisted or otherwise rotated in a counterclockwise direction (as shown in the drawings) they will be driven into the sclera of the eye for temporary fixation. Prongs 27 and 28 may also be curved in directions opposite to that shown so that fixation can alternatively be accomplished by clockwise rotation. A slot 29 is provided at the top of the shaft 25 in order to receive the head of a micro screwdriver so that the surgeon may effect counterclockwise rotation or twisting of the fixator. In order to accomplish proper fixation of the fixator to the sclera it is necessary for the prongs 27 and 28 to enter the sclera almost simultaneously. Accordingly the longitudinal axis of the fixator shaft 25 should be arranged substantially perpendicular to the plane of the sclera at the point of entry of the prongs. Since however the securing devices 21 are carried about the ring 20 it is necessary for the threaded cylinder 22 to be carried by sleeve 23 on the ring 20 so that it can be pivotally adjusted about the diametric axis of the ring 20 so that the longitudinal axis of the shaft 25 can be placed as desired.

Once the surgeon twists the fixator through approximately one quarter to one half revolution and the prongs 27 and 28 enter the sclera it is necessary for the fixator to be held in the twisted position so that it will not untwist causing the ring to be unsecure. This is accomplished by providing non slip threads 26 on the shaft 25 of the fixator. A variety of different types of non slip threads can be used however the most convenient type are those which simply require the application of a rotatable force to the shaft before any movement of the shaft within the cylinder can be effected.

In use, the surgeon will simply place the ring 20 in the desired location circumventing the cornea of the eye and through the use of a micro screwdriver and slight hand pressure effect twisting of each of the fixators in the securing devices 21. Once twisted, the non-slip threads will prevent untwisting and the ring will be secured in place holding the eye in a stable position.

Because the threaded cylinder 22 is carried on the ring 20 by sleeve 23 a pair of raised portions 31 can be provided on the ring 20 on opposite sides of each of the sleeves 23 to prevent circumferential movement of each securing device along the ring.

While the present invention has been described and illustrated with respect to a certain preferred embodiment which produces satisfactory results, it will be appreciated by those skilled in the art, after understanding the purposes of the invention, that various other changes and modifications may be made without departing from the spirit and scope of the invention, and it is therefore intended to cover all such changes and modifications in the appended claims.

What is claimed is:

1. An ophthalmological surgical instrument for stabilizing an eye during ophthalmic surgery comprising, a ring adapted to be placed on the eye surrounding the cornea of the eye, and a plurality of securing devices permanently carried by said ring and circumferentially spaced thereabout for temporarily securing said ring to the surface of said eye so that said ring supports the integrity of the eye regardless of incisions made therein, each securing device includes support means permanently connected to said ring, and a twist fixator carried by said support means for axial movement therethrough to effect temporary fixation of said ring to the surface of the eye, said support means comprising an internally threaded cylinder pivotally connected to said ring, said twist fixator having external threads and thus carried by said threaded cylinder for axial movement therethrough upon rotational movement of said fixator, said external threads of said fixator being non-slip threads to prevent undesired rotational movement of said fixator in said cylinder.

2. The ophthalmological surgical instrument according to claim 1 wherein said securing devices are equally spaced about said ring.

3. The ophthalmological surgical instrument according to claim 2 wherein there are four securing devices placed at approximately 90° intervals circumferentially about said ring.

4. The ophthalmological surgical instrument according to claim 1 wherein said twist fixator carries a pair of prongs axially extending in a curved direction so that upon rotational movement of said fixator within said cylinder said prongs will pierce the surface of the eye when said ring is placed in position on the eye for use.

5. The ophthalmological surgical instrument according to claim 4 further comprising a slot carried in said fixator for receiving means to effect rotational movement of said fixator within said cylinder.

6. The ophthalmological surgical instrument according to claim 5 further comprising a sleeve connected to said threaded cylinder extending about said ring for pivotal attachment of said cylinder to said ring.

7. The ophthalmological surgical instrument according to claim 6 further comprising stop means on the surface of said ring to prevent circumferential movement of said sleeve there along.

* * * * *